United States Patent
Prescott et al.

(10) Patent No.: US 9,603,855 B2
(45) Date of Patent: Mar. 28, 2017

(54) INJECTABLE OSTEOGENIC FORMULA AND METHOD OF USING SAME

(71) Applicants: Sandy Marks, Westborough, MA (US); Albert G. Prescott, Westford, MA (US); Paul Odgren, Princeton, MA (US)

(72) Inventors: Albert G. Prescott, Westford, MA (US); Paul Odgren, Princeton, MA (US); Sandy Marks, Westborough, MA (US)

( * ) Notice: Subject to any disclaimer, the term of this patent is extended or adjusted under 35 U.S.C. 154(b) by 0 days.

(21) Appl. No.: 14/504,775

(22) Filed: Oct. 2, 2014

(65) Prior Publication Data
US 2015/0018423 A1   Jan. 15, 2015

Related U.S. Application Data

(62) Division of application No. 11/426,097, filed on Jun. 23, 2006, now abandoned.

(60) Provisional application No. 60/693,391, filed on Jun. 23, 2005.

(51) Int. Cl.
| | | |
|---|---|---|
| A61K 31/5575 | (2006.01) | |
| A61K 31/557 | (2006.01) | |
| A61K 31/728 | (2006.01) | |
| A61K 38/16 | (2006.01) | |
| A61K 9/00 | (2006.01) | |
| A61K 47/36 | (2006.01) | |

(52) U.S. Cl.
CPC ........ *A61K 31/5575* (2013.01); *A61K 9/0019* (2013.01); *A61K 31/557* (2013.01); *A61K 31/728* (2013.01); *A61K 38/16* (2013.01); *A61K 47/36* (2013.01)

(58) Field of Classification Search
CPC .............. A61K 31/557; A61K 31/5575; A61K 31/728; A61K 38/16; A61K 47/36; A61K 9/0019
See application file for complete search history.

(56) References Cited

U.S. PATENT DOCUMENTS

| | | | |
|---|---|---|---|
| 5,385,738 A * | 1/1995 | Yamahira | A61K 9/0024 264/4.1 |
| 5,941,840 A * | 8/1999 | Court et al. | 602/47 |
| 5,952,006 A * | 9/1999 | Drizen et al. | 424/488 |
| 2005/0171015 A1* | 8/2005 | Crabtree et al. | 514/12 |

FOREIGN PATENT DOCUMENTS

WO   WO 2004071543   *   8/2004   ............. A61L 24/00

OTHER PUBLICATIONS

Miller et al. (Abstract of: Bone 1993; 14(2):143-51).*
Li et al. (Journal of Bone and Mineral Research 2003;18(11):2033-2042).*

* cited by examiner

*Primary Examiner* — Ernst V Arnold
(74) *Attorney, Agent, or Firm* — Brian M. Dingman; Dingman IP Law, PC

(57) ABSTRACT

Formulations and methods for growing bone in a site specific location using an osteogenic molecule such as a prostaglandin, and a delivery vehicle which is preferably a polymer matrix.

4 Claims, No Drawings

INJECTABLE OSTEOGENIC FORMULA AND METHOD OF USING SAME

CROSS REFERENCE TO RELATED APPLICATIONS

This application is a divisional of application Ser. No. 11/426,097 filed on Jun. 23, 2006, which itself claims priority of Provisional application Ser. No. 60/693,391 filed on Jun. 23, 2005, the disclosure of which is incorporated herein by reference.

FIELD OF THE INVENTION

This invention relates to growing bone in a site-specific location.

BACKGROUND OF THE INVENTION

The ability to grow bone at a site-specific location, in a minimally invasive manner, would have a profound impact on the health and quality of life for up to 50 million Americans who suffer bone defects and diseases. These diseases include post craniotomy resorption, periodontal disease, degenerative disk disease, osteoporosis, and aseptic osteolysis. Together, these diseases cost the United States Healthcare System in excess of $124 billion annually.

Cranial

Over 750,000 craniotomies are performed every year in the United States, to treat a variety of disorders including tumors, traumas, vascular lesions, seizures, decompression, cranioplasty, infections, intracranial cysts, and nerve decompression. Despite this, the skull has been one of the most difficult regions in which to use autograft techniques because of the cranium's propensity for resorption. Many materials and methods have been used including autologous bone grafts, metal plates (titanium, tantalum, stainless steel), hydroxyapatite cement, and methylmethacrylate, each with significant drawbacks.

Periodontal Disease.

The most common treatment for periodontal disease and tooth loosening is extraction and dental implantation or dentures. Over 20% of Americans, approximately 56 million people, have periodontal disease. Periodontal disease accounted for 10% of all dental costs in 1985.

Spinal Disorders

Spine disorder treatments are slowly trending toward minimally invasive techniques for penetrating past the muscle tissues surrounding the spine. Despite this, the solutions to degenerative disks (fusion, herniated disk repair and disk replacement) are still highly invasive procedures resulting in extensive surgical trauma and prolonged recovery times. Over 1 million spinal surgeries were performed last year and this number continues to rise.

Joint Replacements

Over ½ million knee and hip replacement surgeries are performed in the United States every year. The typical age of these patients is 65 years despite the fact that the average age of pain symptom onset is 40 years. The reason for this disparity is that the implants cause bone resorption at the interface, making their maximum useful life less than 15 years.

Overall, the ability to induce rapid, localized bone growth would have a substantial beneficial effect in all the above conditions by reducing morbidity, hospitalization time, recovery time, and costs. The ability to grow bone at specific sites would also have a substantial positive impact on the treatment of bone fractures resulting from osteoporosis. It is estimated that over 24 million people suffer from osteoporosis, resulting in 3 million fractures per year in the United States. In 1995 osteoporotic fractures were estimated at $13.8 billion in direct medical expenses.

| Disorder | Annual U.S. Cases |
| --- | --- |
| Craniotomies | 750,000 |
| Periodontal Disease | 28,000,000 |
| Spinal Surgeries | 1,000,000 |
| Aseptic Osteolysis | 500,000 |
| Osteoporosis | 3,000,000 |
| Total | 33,250,000 |

Bone Morphogenic Proteins (BMPs) are osteogenic compounds. However, BMPs can cause ectopic ossification, making them somewhat difficult and risky to use.

SUMMARY OF THE INVENTION

The invention comprises formulations and methodologies for treating degenerative bone conditions, bone fractures, and other bone-related conditions by combining an osteogenic compound with a delivery vehicle. The resulting combination may be injected or otherwise applied to (such as by an implant or other device, or by applying it to a site during surgery) a specific site, and cause bone growth at that site.

This invention features an osteogenic formulation comprising an osteogenic compound and a delivery vehicle. The osteogenic compound is preferably prostaglandin (PGE), and may comprise PGE1 and/or PGE2. One reason that prostaglandins are the preferred osteogenic compounds for the invention is that they do not induce bone synthesis at ectopic sites by non-bone cells.

The delivery vehicle may comprise a biodegradable matrix, which preferably comprises one or more polymers. Two preferred polymers are hyaluronic acid or a salt thereof, and/or a poly-glutamic acid.

The invention also features a method of employing an osteogenic compound, comprising providing prostaglandin (PGE) osteogenic compound, providing a biodegradable polymer matrix delivery vehicle for the PGE, mixing the PGE and the delivery vehicle, and delivering the mixture to a site. The PGE may comprise PGE1 and/or PGE2. The polymer preferably comprises hyaluronic acid or a salt thereof, and/or a poly-glutamic acid. The delivery is preferably accomplished with a syringe, but as described above can be accomplished by other know means for site-specific delivery of a treatment vehicle.

DETAILED DESCRIPTION OF THE PREFERRED EMBODIMENTS

The following is a description of the preferred embodiments of the invention. The half-life of prostaglandin E1 (PGE1) is measured in minutes. PGE1 is rapidly metabolized in the lungs, therefore the delivery method is critical to widespread commercial use of PGE1 as an osteogenic compound. The invention is designed to stabilize and hold PGE1, which is by far the most potent osteogenic agent discovered to date, and deliver it via a gelatinous polymer matrix of hyaluronic acid, a material that is itself modestly osteogenic. PGE2 is less osteogenic than PGE1 but may still be useful in the invention. The matrix allows the osteogenic compound (preferably a prostaglandin) to make physical contact with the targeted bone surface, thus stimulating only the cells required for the healing process. The matrix releases the compound over a period of time so that the stimulation of the cells is maintained over a period of time until the process of osteogenesis is completed. Both the matrix and the compound are reabsorbed by the body. Because the material may be delivered by a syringe, more than one treatment can be readily accomplished. No surgical procedures are required.

The delivery matrix is a biodegradable polymer. The polymer should be gelatinous in nature and water soluble. This includes polymers such as carboxymethylcellulose, poly-glutamic acid (PGA), but preferably the polymer is hyaluronic acid. Hyaluronic acid is biocompatible and is itself mildly osteogenic.

The following are examples of producing the various preferred formulations.

Example of Preferred Formulation

PGE1 is dissolved in pure water. In the event that the PGE1 won't completely dissolve, pure ethanol may be added until all the PGE1 is dissolved. The concentration of PGE1 may be varied as necessary.

Hyaluronic acid is hydrated in pure water. Hyaluronic acid concentrations may also be varied, but a concentration of greater than 30 mg/ml in pure water works well and may thus be diluted with the PGE1 solution.

The PGE solution is combined with the hyaluronic acid gel and allowed to mix. Mixing may be achieved in a mixer, a beaker with a stir bar and magnetic stirrer, or even by coupling two syringes together, each containing one of the two solutions. Solutions should be mixed until homogeneous. In addition, salts of hyaluronic acid may be used to vary the release of the PGE1. Sodium hyaluronate, calcium hyaluronate, and even ferric hyaluronate may be used. As the valence of the counter cation increases (i.e., Na+, Ca++, Fe+++ and so forth) the half life of hyaluronate increases, and the release rate of PGE1 decreases.

Following are examples of purified hyaluronic acid and poly-gamma-glutamic acid that may be produced for use as the matrix for the invention.

Example of Hyaluronic Acid Purification

1. Rooster combs are sliced and placed in ethanol. The ethanol is changed daily until it is no longer cloudy. Three days, 6 liters ethanol used.

2. The ethanol is drained and the combs are placed in water with an antiseptic (Thymol) to prevent microbial growth.

3. The combs are mixed at less than 10° C. overnight or until the solution viscosity exceeds 500 cps. Steps 2 and 3 together take 3 days and use no ethanol.

4. The combs are strained from the extract. The extract is treated with NaCl to a final concentration of 0.2M.

5. The extract is centrifuged and added to 3 volumes of ethanol and the resulting stringy white precipitate is removed and stored under ethanol. Steps 4 and 5 together take 1 day and use 3 liters ethanol.

6. Dissolve precipitate in DI water to approximately 1.5 mg/ml concentration. Though the actual concentration will change later, 0.75 to 5.0 mg/ml HA may be successfully precipitated with ethanol (and NaCl).

7. Add 100 ml of chloroform to every 1 liter of solution, mix overnight and centrifuge for 5 minutes at 4,000 RPMs. This step removes residual fats, lipids, certain proteins and other materials that have been found to inhibit the Pronase® step. Steps 6 and 7 together take 2 days and use no ethanol.

8. Add the aqueous portion to a temperature-controlled reactor, add an antiseptic (Thymol), <0.5 mM $CaCl_2$, heat to 37° C., adjust pH to 8.0 and add Pronase®. These are optimum Pronase® conditions per CalBiochem, Pronase® manufacturers.

9. Maintain pH at 8.0 via pH control and the addition of 0.2M Tris buffer. Run until no more Tris is required (typically overnight). This hydrolyzes proteins not removed by chloroform, as well as the link proteins responsible for binding HA to other GAG's. Steps 8 and 9 together take 1 day and use no ethanol.

10. Make up a solution of 100 mls of 2% CPC and 0.3M NaCl. Adjust the reactor contents to 0.3M, and add the CPC/NaCl solution to the reactor. It will change color from opaque to yellow. Allow it to mix for 15 minutes. Filter the reactor contents through a membrane filter (0.2 micron PES filter) and collect in a flask. This causes DNA, chondriotin sulfate, heparin and other non-HA GAG's to complex and precipitate. They are subsequently removed by filtration. This step takes one-half day, and no ethanol.

11. Using a Pall-Filtron 30 kDa MWCO PES membrane, diafilter the solution against 5 volumes of 0.3M NaCl. This removes amino acids, peptides, Pronase®, CPC and other low MW contaminants.

12. Either precipitate with ethanol and dry under vacuum, or lyophilize the contents of the flask. This is the best way to store material until formulation. Formulation strength cannot be achieved through TFD at this time. Steps 11 and 12 together take one-half day and use 3 liters ethanol.

13. Formulate to 10 mg/ml and verify properties against the traditional process. 10 mg/ml is a simple HA concentration that has been used often in the industry. One day, no ethanol.

The following describes the equipment used for diafiltration:

| DF Parameter | Value |
| --- | --- |
| 1. Three membrane setup (Used to determine MW cutoff for diafiltration) | |
| Membrane Type | Omega Polyethersulfon |
| Channel Depth | 40 mil |
| Membrane Area | 0.045 $ft^2$/channel |
| Number of Channels | 3 in parallel |
| Trans-Membrane Pressure (TMP) | 18.5 psig |
| Pressure drop across membrane | 2.5 psig |
| Cross Flow Rate | 200 ml/min/channel |
| 2. Single membrane DF experimental setup (Used to purify HA from rooster comb) | |
| Membrane Type | Omega Polyethersulfon |
| Membrane Area | 1.0 $ft^2$ |
| Trans-Membrane Pressure (TMP) | 8.0 psig |
| Cross Flow Rate | 1,000 ml/min |
| MWCO | 30k |
| Type | Centramate |
| Configuration | Open Channel |

The pump used to performed the diafiltration was a Cole-Parmer Masterflex®L/S® Precision Standard Tubing Pump capable of over 1700 ml/min, SKU# EW-77911-00.

Example 1

PGA Using Preferred Fermentation Method, and Purification to Medical Grade

*Bacillus licheniformis* ATCC 9945a was grown in Medium E. The fermentation was carried out at small scale, in shake flasks, at 37 C. Aeration was provided by diffusion. When the viscosity stopped rising (typically after about 3-5 days of fermentation), the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.22 microns, to remove the host cells.

The filtrate was neutralized, and buffer exchanged with pure water and concentrated via diafiltration using a filter with a MWCO of 30 kDa. Material from this purification may be sterile filtered.

To describe the process in more detail, when the viscosity stopped rising, the fermentation broth was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kda MWCO pore size. Five diafiltration volumes of solution were processed. At the end, the retentate was collected, sterilized by passing through a 0.22 micron filter, and precipitated in sterile ethanol and stored.

Material from this example has been used in rats in subsequent experiments with no inflammatory response. The molecular weight was determined to be 2 million Daltons using the following analytical MALLS method described in the Stock thesis that is incorporated by reference herein. PGA was dissolved at a concentration of 1 mg/ml in 0.1 M citric acid, pH 2 to 3, with 0.05% sodium azide. The sample was degassed and 0.2 milliliters was injected at a flow rate of 0.5 mls/min. The SEC can utilize a TossoHaas TSK G5000PWXL, G6000PWXL, Waters Ultrahydrogel 1000 or 250. A Dawn DSP laser photometer from Wyatt technologies in conjunction with a Waters differential refractometer is used for detection. This process is capable of making high molecular weight (when measured as described) poly-gamma-glutamic acid at purities up to and including pharmaceutical grade.

Example 2

PGA from Another Commercial Source Purified

A sample reported to be poly-gamma-glutamic acid in excess of 1 million Daltons was received from an offshore commercial supplier. The viscosity of a sample of known concentration seemed to be lower than would be the case if the PGA was indeed of the reported molecular weight. Analysis was impossible due to the large amount of contaminants, as evidenced by the off-white color noted when the sample was hydrated, and the fact that the hydrated sample had an odor similar to fermentation broth.

This material was re-circulated through an Omega Polyethersulfon ultra-filtration cartridge by Pall Corporation with a 0.2 micron pore size. Once collected, the filtrate was re-circulated using an Omega Polyethersulfon ultra-filtration cartridge by Pall Corporation with a 0.16 micron pore size. The filtrate was collected and re-circulated through an Omega Polyethersulfon ultra-filtration cartridge by Pall Corporation with a 30 kda MWCO pore size. Five diafiltration volumes of solution were processed. The resulting material was clear and odorless, supporting the production of low molecular weight, high purity PGA.

Example 3

PGA

*Bacillus licheniformis* ATCC 9945a was grown in Medium E. The fermentation was carried out at small scale, in shake flasks, at 37 C. Aeration was provided by diffusion. When the viscosity stopped rising, the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.16 microns.

The filtrate was neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 4

PGA

*Bacillus licheniformis* ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by passing the broth through a 0.22 micron TFF filter and collecting the filtrate. The filtrate was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 5

PGA

*Bacillus licheniformis* ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by centrifugation at a speed over 10,000×g. The supernatant was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

What is claimed is:
1. A method of employing an osteogenic formulation to grow bone at a specific site in a mammal, comprising:
   a) creating an osteogenic formulation by:
      providing prostaglandin E1 (PGE1);

providing a gelatinous, water-soluble biodegradable 2 million Dalton poly-glutamic acid polymer matrix delivery vehicle for the PGE1;

mixing the PGE1 and the delivery vehicle; and b) delivering the osteogenic formulation to the specific site in mammalian tissue such that the formulation makes contact with a bone surface so as to cause bone growth at the site, wherein both the matrix and the PGE1 are reabsorbed by the body.

2. The method of claim 1 in which delivery is accomplished with a syringe.

3. The method of claim 1 wherein the PGE1 is dissolved in water to create an osteogenic solution that is mixed with the delivery vehicle.

4. The method of claim 3 in which the mixing creates a homogeneous formulation.

\* \* \* \* \*